(12) United States Patent
O'Brien et al.

(10) Patent No.: US 6,479,720 B1
(45) Date of Patent: Nov. 12, 2002

(54) ALKYLAROMATIC PROCESS USING EFFICIENT PREFRACTIONATION

(75) Inventors: Dennis E. O'Brien, Arlington Heights, IL (US); Dennis H. Bielinski; Zhanping Xu, both of Williamsville, NY (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 09/474,973

(22) Filed: Dec. 29, 1999

(51) Int. Cl.$^7$ .............................................. C07C 15/067
(52) U.S. Cl. ........................ 585/448; 585/455; 585/323; 208/354
(58) Field of Search .................. 208/93, 354; 585/448, 585/455, 315, 319, 322, 323

(56) References Cited

U.S. PATENT DOCUMENTS

| | | | |
|---|---|---|---|
| 2,471,134 A | | 5/1949 | Wright ........................ 196/700 |
| 3,950,448 A | * | 4/1976 | Witt ........................ 260/671 B |
| 4,070,408 A | * | 1/1978 | Vickers .................. 260/672 R |
| 4,587,370 A | | 5/1986 | DeGraff ........................ 585/450 |
| 5,109,139 A | * | 4/1992 | Dickson et al. ............. 585/821 |
| 5,289,688 A | * | 3/1994 | Agrawal ........................ 62/24 |
| 5,785,819 A | * | 7/1998 | Kaibel et al. ................ 202/158 |
| 6,069,285 A | * | 5/2000 | Fritsch et al. ............... 585/449 |

OTHER PUBLICATIONS

Triantafyllou, C. et al. "The Design and Optimisation of Fully Thermally Coupled Distillation Columns" *Trans IchemE*, vol. 70, Part A, Mar. 1992 p. 118–132.

Schulz, R.C. et al. "LAB Production" 2$^{nd}$ World Conference on Detergents, Montreux, Switzerland, Oct. 5–10, 1986.

*Handbook of Petroleum Refining Processes* Edited by: Robert A. Meyers (New York, McGraw–Hill, 2$^{nd}$ Edition 1997) pp. 1.53–1.66 and 5.11–5.19 ISBN 0–07–041796–2 TP690.H34.

Nelson, W.L. *Petroleum Refinery Engineering* McGraw–Hill, New York, 1$^{st}$ Ed., 4$^{th}$ Impression, 1936, p. 442, figure 141.

Watkins, R.N. *Petroleum Refinery Distillation* Gulf Publishing Company, Book Division, Houston, 2$^{nd}$ Ed., May 1981, pp. 101–103 and 114–115.

Briones, Victor et al. "Pinch Analysis Used in Retrofit Design of Distillation Units" *Oil and Gas Journal*, Jun. 21, 1999 pp. 41–46.

* cited by examiner

*Primary Examiner*—Bekir L. Yildirim
(74) *Attorney, Agent, or Firm*—John G. Tolomei; James C. Paschall; Michael A. Moore

(57) ABSTRACT

A process for the production of alkylaromatic hydrocarbons by alkylating aromatic hydrocarbons with linear olefinic hydrocarbons is disclosed. The linear olefinic hydrocarbons are produced by dehydrogenating linear paraffinic hydrocarbons which are extracted from a heartcut that is distilled from a kerosene boiling range fraction in either a dividing wall fractionation column or in two fully thermally coupled fractionation columns. The process significantly decreases the cost of utilities in producing alkylaromatic precursors for detergent manufacture.

23 Claims, 3 Drawing Sheets

US 6,479,720 B1

ALKYLAROMATIC PROCESS USING EFFICIENT PREFRACTIONATION

FIELD OF THE INVENTION

This invention is an improvement in a process for the production of alkylated aromatic compounds.

BACKGROUND OF THE INVENTION

Nearly forty years ago, it became apparent that household laundry detergents made of branched alkylbenzene sulfonates were gradually polluting rivers and lakes. Solution of the problem led to the manufacture of detergents made of linear alkylbenzene sulfonates (LABS), which were found to biodegrade more rapidly than the branched variety. Today, detergents made of LABS are manufactured worldwide.

LABS are manufactured from linear alkyl benzenes (LAB). The petrochemical industry produces LAB by dehydrogenating linear paraffins to linear olefins and then alkylating benzene with the linear olefins in the presence of HF. The linear paraffins are straight chain (unbranched) or normal paraffins. Normally, the linear paraffins are a mixture of linear paraffins having different carbon numbers. The linear paraffins have generally from about 6 to about 22, preferably from 10 to 15, and more preferably from 10 to 12 or from 11 to 13, carbon atoms per molecule.

A preferred method of production of the linear paraffins is the extraction of straight chain hydrocarbons from a hydrotreated kerosene boiling range petroleum fraction. The kerosene boiling range fraction contains a mixture of different hydrocarbons, including mostly paraffinic and aromatic hydrocarbons, but containing also olefinic and naphthenic hydrocarbons. The kerosene boiling range fraction is usually defined as comprising a fraction having a boiling range of from about 300° F. (149° C.) to about 572° F. (300° C.). The initial boiling point of the kerosene boiling range fraction may vary from about 300 to about 374° F. (149 to 190° C.) and the final boiling point may vary from about 455 to about 572° F. (235 to 300° C.). The kerosene boiling range generally includes hydrocarbons having from about 8 to about 17 carbon atoms.

The kerosene boiling range fraction is generally produced by fractionating crude oil. Crude oil is the liquid part, after being freed from dissolved gas, of petroleum, a natural organic material composed principally of hydrocarbons that occur in geological traps. Being derived from a natural material, crude oils vary in composition depending on where the petroleum occurred and other factors. Commercial oil refineries typically receive crude oil from many different sources, and the composition of the crude oil that is charged to the crude oil fractionation unit changes frequently. The paraffinic and aromatic hydrocarbons that make up the bulk of a kerosene boiling range fraction can change as different crude oils are processed in the crude oil fractionation unit. It is common for the volumetric flow rate of the kerosene boiling range fraction to fluctuate by up to 30 vol-% or more, for a given boiling point range of the kerosene boiling range fraction produced from a crude oil fractionation unit. Because such fluctuations in flow rate can make it difficult to control downstream units that process the kerosene boiling range fraction, the operator of a crude oil fractionation unit may intentionally adjust the initial and final boiling points of the kerosene boiling range fraction as permissible within the above mentioned ranges and thereby achieve a more constant flow rate of the kerosene boiling range fraction. It is also common for the kerosene boiling range fraction to fluctuate between liquid phase and a mixture of vapor and liquid phases, since the proportion of vapor phase depends on both the composition of the kerosene boiling range fraction and its temperature, which can also vary. For a given temperature, the lighter the kerosene boiling range fraction, the greater is the proportion in the vapor phase. Accordingly, in commercial practice the composition, the amount, the boiling range and/or the phase of the kerosene boiling range fraction recovered from a commercial crude oil fractionation unit often fluctuate daily, or even hourly.

In order to produce LAB having, for example, from 11 to 13 carbon atoms per linear alkyl group, a stream of linear paraffins comprising $C_{11}$ to $C_{13}$ hydrocarbons is desired. A suitable stream is a heartcut of the kerosene boiling range fraction suffices, provided that hydrocarbons boiling lower than $C_{11}$ linear paraffins and hydrocarbons boiling higher than $C_{13}$ linear paraffins must be removed from the kerosene fraction. Generally, this heartcut is produced in a two-step, strip-and-rerun fractionation process. First, the kerosene fraction is introduced into a fractionation column, called a stripper column, which strips overhead the $C_{10}-$ hydrocarbons from the kerosene feedstock, producing a bottom stream comprising $C_{11}+$ hydrocarbons. Then, the bottom stream is introduced into a second fractionation column, called a rerun column, which boils overhead the $C_{11}$ to $C_{13}$ hydrocarbons as a heartcut and produces a bottom stream comprising $C_{14}+$ hydrocarbons. In some commercial units, the overhead condenser of the second fractionation column is a contact condenser. This heartcut is then hydrotreated, and the straight chain hydrocarbons are extracted from the hydrotreated fraction, thereby producing the linear paraffin stream.

Alkylaromatic processes that use the two-step, strip-and-rerun fractionation process to produce the heartcut are inefficient, since they require relatively large amounts of utilities. Thus, alkylation processes are sought in which the heartcut is produced in a more efficient manner that uses fewer utilities than the prior art process.

Over fifty years ago, Wright proposed replacing two distillation columns with a single distillation column having a vertical partition (dividing wall column) within the column that would effect the separation of the column feed into three constituent fractions. It was recognized then that a dividing wall column could minimize the size or cost of the equipment needed to produce overhead, bottoms, and sidedraw products. See U.S. Pat. No. 2,471,134 (Wright). Wright described using the dividing wall column to separate a mixture of ethane, propane, butanes, and a small amount of $C_5$ and heavier hydrocarbons.

Since then, researchers have studied the dividing wall column and have proposed using dividing wall columns for separating other mixtures, including xylenes (Int. Chem. Engg., Vol. 5, No. 3, July 1965, 555–561); butanes and butenes (See e.g., Trans IChemE, Vol.70, Part A, March 1992, 118–132); methanol, isopropanol, and butanol (See e.g., Trans IChemE, Vol. 72, Part A, September 1994, 639–644); ethanol, propanol, and butanol (Ind. Eng. Chem. Res. 1995, 34, 2094–2103); air (See e.g., Ind. Eng. Chem. Res. 1996, 35, pages 1059–1071); natural gas liquids (Chem. Engg., July 1997, 72–76); and benzene, toluene, and ortho-xylene (Paper No. 34 K, by M. Serra et al., prepared for presentation at the AIChE Meeting, Los Angeles, Calif., U.S.A., November 1997). The Serra et al. paper also describes separating mixtures of butanes and pentane; pentanes, hexane, and heptane; and propane and butanes.

Despite the advantages of the dividing wall column and despite much research and study, the processing industry has long felt reluctant to use dividing wall columns in commercial processes. This widespread reluctance has been attributed to various concerns, including control problems, operational problems, complexity, simulation difficulties, and lack of design experience. See, for example, the articles by C. Triantafyllou and R. Smith in Trans IChemE, Vol. 70, Part A, March 1992, 118–132; F. Lestak and C. Collins in Chem. Engg., July 1997, 72–76; and G. Duennebier and C. Pantelides in Ind. Eng. Chem. Res. 1999, 38, 162–176. The article by Lestak and Collins sets forth some general guidelines and considerations when substituting a dividing wall column for conventional columns. Nevertheless, the literature documents relatively few practical uses of dividing wall columns in commercial plants. See the article by H. Rudd in The Chemical Engineer, Distillation Supplement, Aug. 27, 1992, s14–s15 and the article in European Chemical News, Oct. 2–8, 1995, 26.

Prior art alkylaromatic processes, in particular, do not use dividing wall distillation columns. Nor do they use fully thermally coupled distillation columns, which as explained in the above-mentioned article by C. Triantafyllou and R. Smith, are thermodynamically equivalent to dividing wall columns when there is no heat transfer across the dividing wall. In particular, a dividing wall distillation column has not been used for producing the heartcut from the kerosene boiling range fraction. This is not only for the reasons given above but also for three additional reasons. First, the focus of prior research studies has been on separating relatively unchanging mixtures of only a few (e.g., 3 to 5) components, whereas the kerosene boiling range fraction is a seemingly ever-changing mixture of hundreds or thousands of hydrocarbons. Second, the research studies produce dividing wall distillation product streams containing usually only one component, whereas the heartcut, stripper overhead stream, and rerun bottom stream contain many hydrocarbon components. Third, product specifications for LAB require that the heartcut composition be controlled relatively tightly, since the detergent properties of the linear alkylbenzene sulfonates (LABS) depend in large part on the particular paraffin isomers in the heartcut. Thus, alkylaromatic processes are characterized by both an ever-changing composition of a complex kerosene mixture and a relatively tight specification on a complex mixture of paraffins in the heartcut. This combination compounds the problems, difficulties, and complexity of using a dividing wall distillation column or two fully thermally coupled distillation columns.

SUMMARY OF THE INVENTION

This invention is a process for the production of alkylaromatic hydrocarbons by alkylating feed aromatic hydrocarbons with linear olefinic hydrocarbons, where the linear olefinic hydrocarbons are produced by dehydrogenating linear paraffinic hydrocarbons, where the linear paraffinic hydrocarbons are extracted from a heartcut, and where the heartcut is fractionated from a kerosene fraction in either a dividing wall fractionation column or in two fully thermally coupled fractionation columns, where the two fully thermally coupled fractionation columns are a prefractionator and a main column. It has now been recognized that use of two fully thermally coupled fractionation columns or of a dividing wall fractionation column produces the heartcut in a manner that is stable and controllable for commercial LAB production, despite the complexity of the mixture of hydrocarbons in commercial kerosene fractions and despite the fluctuations in the compositions of those fractions. In addition, use of two fully thermally coupled fractionation columns or the dividing wall fractionation column reduces significantly the cost of utilities in producing the heartcut. In a preferred embodiment of this invention, the two fully thermally coupled fractionation columns or the dividing wall fractionation column is integrated with the paraffin recycle fractionation column and/or the LAB product fractionation column, thereby further decreasing the cost of utilities for producing LAB. As between a single dividing wall fractionation column on the one hand and two fully thermally coupled fractionation columns on the other hand, the former is preferred when the cost of a single fractionation vessel represents a significant savings over that of two fractionation vessels.

Accordingly, in a broad embodiment, this invention is a process for the production of alkylaromatics. A feed stream comprising low-boiling hydrocarbons, heartcut hydrocarbons, and high-boiling hydrocarbons passes into a first lateral section of an intermediate portion of a fractionation column at fractionation conditions. The entering compounds are separated to provide an overhead stream comprising the low-boiling hydrocarbons, a sidedraw stream comprising the heartcut hydrocarbons, and a bottom stream comprising the high-boiling hydrocarbons. The first lateral section is separated from a second lateral section of the fractionation column by a vertically oriented baffle extending upward from a lower portion of the fractionation column to an upper portion of the fractionation column. The overhead stream is at least partially condensed to form a condensed stream comprising the low-boiling hydrocarbons, and a portion of the condensed stream is refluxed to the fractionation column. The low-boiling hydrocarbons are recovered from the overhead stream. Heat is introduced to the lower portion of the fractionation column, and a bottom stream comprising the high-boiling hydrocarbons is withdrawn from the lower portion of the fractionation column. The high-boiling hydrocarbons are recovered from the bottom stream. A sidedraw stream comprising the heartcut hydrocarbons comprising paraffinic hydrocarbons is withdrawn from the second lateral section of the fractionation column. At least a portion of the sidedraw stream passes to a dehydrogenation zone to dehydrogenate the paraffinic hydrocarbons to monoolefinic hydrocarbons. A dehydrogenation zone effluent stream comprising the monoolefinic hydrocarbons is recovered from the dehydrogenation zone. At least a portion of the dehydrogenation zone effluent stream and an aromatic stream comprising a feedstock aromatic compound pass to an alkylation zone. The alkylation zone is operated at alkylation conditions to alkylate the feedstock aromatic compound with the monoolefinic hydrocarbons to produce alkylaromatic hydrocarbons. An alkylation effluent stream comprising the alkylaromatic hydrocarbons is recovered from the alkylation zone.

In another broad embodiment, this invention is a process for the production of alkylaromatics. A feed stream comprising low-boiling hydrocarbons, heartcut hydrocarbons, and high-boiling hydrocarbons passes into a prefractionator fractionation column which separates the entering hydrocarbons to provide a prefractionator overhead vapor stream comprising the low-boiling hydrocarbons and the heartcut hydrocarbons and a prefractionator bottom liquid stream comprising the high-boiling hydrocarbons and the heartcut hydrocarbons. At least a portion of the prefractionator overhead vapor stream passes to a main fractionation column, which is fully thermally coupled to the prefractionator fractionation column. At least a portion of the prefractionator bottom liquid stream passes to the main fractionation column. Hydrocarbons are separated in the main fractionation column. The following five streams are recovered from the main fractionation column: a main column overhead stream comprising the low-boiling hydrocarbons, a main column bottom stream comprising the high-boiling hydrocarbons, a main column product sidedraw stream comprising the heartcut hydrocarbons, a main column upper sidedraw stream comprising the low-boiling hydrocarbons and the heartcut hydrocarbons, and a main column lower sidedraw stream comprising the heartcut hydrocarbons and the high-boiling hydrocarbons. At least a portion of the main column upper sidedraw stream passes to the prefractionator fractionation column. At least a portion of the main column lower sidedraw stream passes to the prefractionator fractionation column. The main column overhead stream is at least partially condensed to form a condensed stream comprising the low-boiling hydrocarbons. A portion of the condensed stream is refluxed to the main fractionation column. Low-boiling hydrocarbons are recovered from the main column overhead stream. Heat is introduced to a lower portion of the main fractionation column, the high-boiling hydrocarbons are recovered from the main column bottom stream. At least a portion of the main column product sidedraw stream passes to a dehydrogenation zone, where the paraffinic hydrocarbons are dehydrogenated to monoolefinic hydrocarbons. A dehydrogenation zone effluent stream comprising the monoolefinic hydrocarbons is recovered from the dehydrogenation zone. At least a portion of the dehydrogenation zone effluent stream and an aromatic stream comprising a feed aromatic hydrocarbon pass to an alkylation zone operated at alkylation conditions to alkylate the feed aromatic hydrocarbon with the monoolefinic hydrocarbons to produce an alkylation effluent stream comprising alkylaromatic hydrocarbons. The alkylaromatic hydrocarbons are recovered from the alkylation effluent stream.

Other embodiments of the invention are set forth in the detailed description of the invention.

INFORMATION DISCLOSURE

Figure 1:
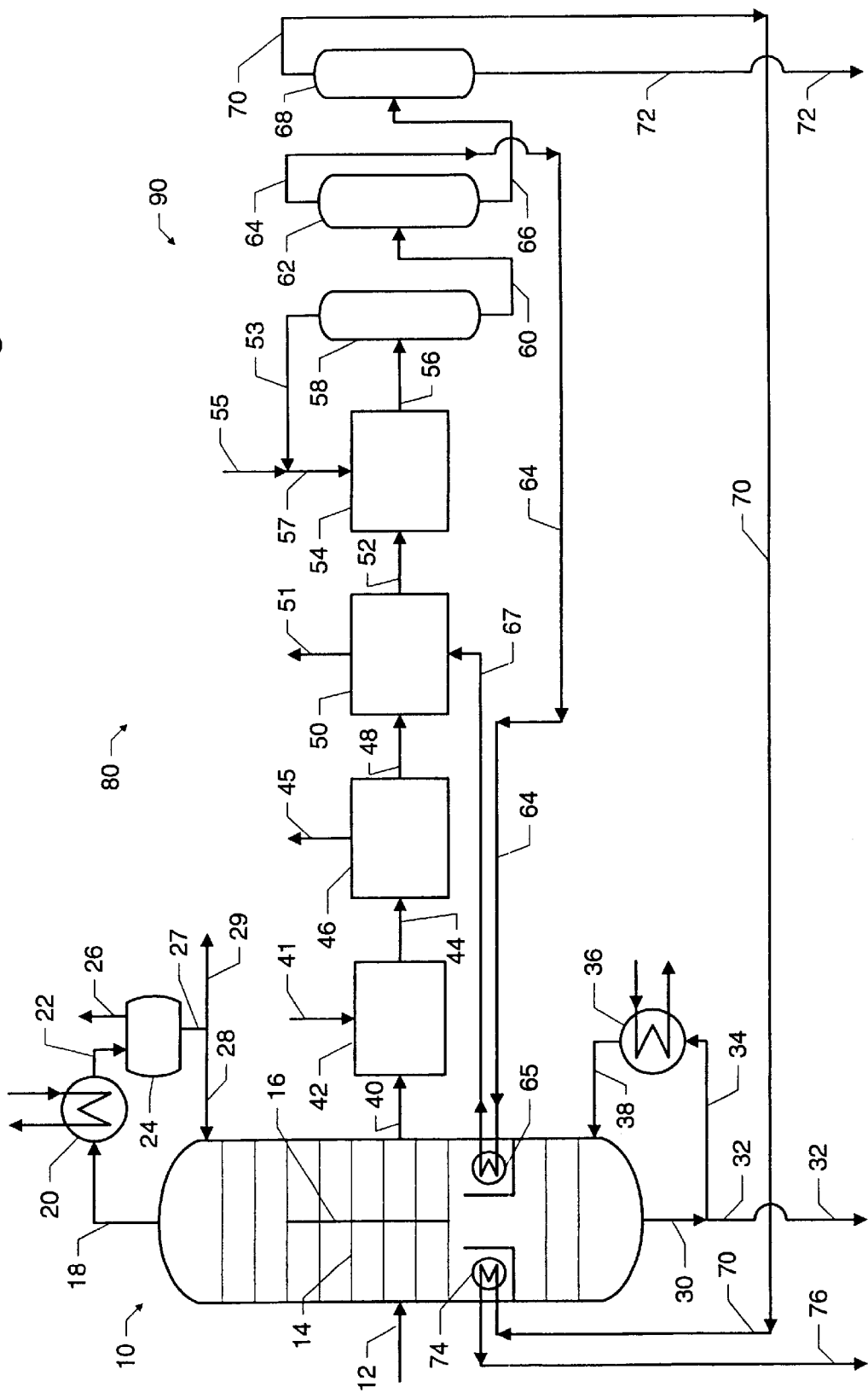
FIGS. 1–3 are process flow diagrams, each depicting an embodiment of the invention.

U.S. Pat. No. 2,471,134 (Wright) discloses a vertical fractionation column having a vertical partition that separates the feed inlet and a side stream outlet.

The article by C. Triantafyllou and R. Smith in Trans IChemE, Vol. 70, Part A, March 1992, starting at page 118 explains that a dividing wall distillation column is thermodynamically equivalent to a fully thermally coupled distillation column, provided that there is no heat transfer across the dividing wall.

The paper entitled *LAB Production*, by R. C. Schulz, P. R. Pujado, and B. V. Vora, presented at the 2$^{nd}$ World Conference on Detergents, held at Montreux, Switzerland, during Oct. 5–10, 1986, describes an LAB process wherein feed treatment of the kerosene consists of prefractionation using a stripper and a rerun column followed by hydrotreating of the kerosene heartcut. The teachings of the Schulz et al. article are incorporated herein by reference. LAB processes are further described in the book edited by Robert A. Meyers entitled *Handbook of Petroleum Refining Processes*, (McGraw-Hill, New York, Second Edition, 1997) at Chapter 1.5, the teachings of which are incorporated herein by reference. Paraffin dehydrogenation processes are described in the Meyers book in Chapter 5.2, the teachings of which are incorporated herein by reference.

U.S. Pat. No. 4,587,370 (DeGraff) discloses a fractionation method that uses three fractionation columns employed in series for recovering product alkylaromatics produced by alkylation of feed aromatics. The overhead stream of the second column contains the product alkylaromatics and is employed as the heat source for the reboiler of the first column, which recycles feed aromatics to the alkylation reactor.

The book entitled "Petroleum Refinery Engineering," written by W. L. Nelson, and published by McGraw-Hill Book Company, Inc., New York, First Edition, Fourth Impression, 1936, page 442, FIG. 141, shows a method of removing reflux heat using circulating reflux.

The book entitled, "Petroleum Refinery Distillation," written by R. N. Watkins, and published by Gulf Publishing Company, Book Division, Houston, Tex., Second Edition, May, 1981, pages 101–103 and 114–115, describes vacuum towers with pumpback and pumparound reflux heat removal.

The article written by Victor Briones, et al., which was published in Oil and Gas Journal, Jun. 21, 1999, beginning at page 41, describes using a pinch analysis method to design heat integration between atmospheric and vacuum units in a crude oil unit.

DETAILED DESCRIPTION

The feed to this invention is a kerosene boiling range fraction. A preferred feed has an initial boiling point of from about 311° F. to about 374° F. (155 to 190° C.) and a final boiling point of from about 455° F. to about 520° F. (235 to 271° C.). Preferred hydrocarbons in the feed have from about 10 to about 15 carbon atoms. The content of the normal paraffins, a desirable component of the feed when producing LAB, can vary generally from about 15 to about 35 vol-% of the feed, but is preferably greater than 20 vol-% and more preferably greater than 25 vol-%. The feed is preferably a two-phase, vapor-liquid mixture comprising from about 5 to about 30 mol-% vapor phase. The temperature of the feed is generally from about 365 to about 430° F. (185 to 221° C.), and preferably from about 400 to about 420° F. (204 to 216° C.).

The description that follows is written in terms of fractionating a feed stream of hydrocarbons into a light stream comprising low-boiling hydrocarbons, a sidedraw or product stream comprising heartcut hydrocarbons, and a heavy stream comprising high-boiling hydrocarbons. Low-boiling hydrocarbons generally have a lower boiling point than the heartcut hydrocarbons and typically contain at least one fewer carbon atom than the heartcut hydrocarbons. High-boiling hydrocarbons generally have a higher boiling point than the heartcut hydrocarbons and typically contain at least one more carbon atom than the heartcut hydrocarbons. The feed stream typically has a concentration of low-boiling hydrocarbons of more than 5 wt-%, a concentration of heartcut hydrocarbons of more than 50 wt-%, and a concentration of high-boiling hydrocarbons of more than 5 wt-%.

The light stream, the sidedraw stream, and the heavy stream are fractions defined by their boiling range, since each fraction contains tens, hundreds, or more components. The light stream is a stream in which generally at least 50 vol-%, and typically at least 75 vol-%, of the stream lies within the boiling range of from 240° F. (116° C.) to 340° F. (171° C.). At least 50 vol-%, and typically at least 75 vol-%, of the sidedraw stream lies within the boiling range of from 360° F. (182° C.) to 460° F. (238° C.). For the heavy stream, at least 50 vol-%, and typically at least 75 vol-%, of the stream lies within the boiling range of from 470° F. (243° C.) to 850° F. (454° C.). These boiling ranges are determined by ASTM Method D-86, and the vol-%'s are measured as a liquid. In producing these fractions, this invention is in contrast to the distillation research studies of the prior art, where the streams produced by the distillation usually contain one or a small number of components which are usually measured individually. As used herein, the term "fractionation" thus is used to refer to separation into boiling range fractions such as these, whereas the term "distillation" is used to refer to the prior art's separation of a stream into a small number of components. The arrangement of the dividing wall fractionation column and any associated equipment and its operating conditions (e.g., temperatures and vapor/liquid ratios) in the description that follows will be those generally associated with accomplishing such a separation in accordance with this invention, and are not intended to limit the scope of the invention as set forth in the claims.

A common example of a separation that can be accomplished using the subject invention is the separation of a feed comprising $C_9$ to $C_{15}$ hydrocarbons into a light stream comprising low-boiling hydrocarbons comprising $C_9$ and $C_{10}$ hydrocarbons, a sidedraw stream comprising heartcut hydrocarbons comprising $C_{11}$ $C_{12}$, and $C_{13}$ hydrocarbons, and a heavy stream comprising high-boiling hydrocarbons comprising $C_{14}$ and $C_{15}$ hydrocarbons. In this example, the light key component, which is the lightest component in the sidedraw stream, is typically normal $C_{11}$ paraffin, and the heavy key component, which is the heaviest component in the sidedraw stream, is typically normal $C_{13}$ paraffin. If the feed also contains hydrocarbons lighter than $C_9$ hydrocarbons, then the low-boiling hydrocarbons can also comprise hydrocarbons lighter than $C_9$ hydrocarbons. If the feed contains hydrocarbons heavier than $C_{15}$ hydrocarbons, then the high-boiling hydrocarbons can comprise other hydrocarbons heavier than $C_{14}$ hydrocarbons in addition to the $C_{15}$ hydrocarbons. Another example is the separation of a feed comprising hydrocarbons lighter than $C_8$ hydrocarbons, $C_8$ to $C_{15}$ hydrocarbons, and hydrocarbons heavier than $C_{15}$ hydrocarbons. Using this invention, a light stream comprising low-boiling hydrocarbons comprising $C_9$ and lighter hydrocarbons, a sidedraw stream comprising heartcut hydrocarbons comprising $C_{10}$, $C_{11}$, and $C_{12}$ hydrocarbons, and a heavy stream comprising high-boiling hydrocarbons comprising $C_{13}$ and heavier hydrocarbons can be produced. Typically, in this case, the light key component is normal $C_{10}$ paraffin and the heavy key component is normal $C_{12}$ paraffin.

Despite fluctuations in the flow rate, composition, and phases of the feed, it has now been recognized that, when producing LAB, two fully thermally coupled fractionation columns or a dividing wall fractionation column is suitable for producing the heartcut fraction from the feed. Since the capital cost of a single new dividing wall fractionation column is generally less than that of two new fully thermally coupled fractionation columns, the use of a dividing wall fractionation column will be described first, followed by a description of the use of two fully thermally coupled fractionation columns.

When using a dividing wall fractionation column, the heartcut fraction is withdrawn from the dividing wall fractionation column in a sidedraw stream. The dividing wall fractionation column also produces an overhead stream comprising hydrocarbons that have lower boiling points than hydrocarbons in the sidedraw stream and a bottom stream comprising hydrocarbons having higher boiling points than hydrocarbons in the sidedraw stream. The dividing wall fractionation column has one inlet for the feed and three outlets, one outlet for each of the overhead stream, the sidedraw stream, and the bottom stream.

The dividing wall fractionation column has three fractionation zones, a top zone, a middle zone, and a bottom zone. The middle zone contains a dividing wall, the plane of which is vertically oriented. As used herein, the phrase "vertically oriented" means forming an angle with the horizontal of generally between about 85 and about 95 degrees, and preferably between about 87.5 and 92.5 degrees. The longitudinal axis of the middle zone is also generally vertical, as are the longitudinal axes of the top and bottom zones. The dividing wall divides the middle zone into two portions, a feed-side portion and a sidedraw-side portion. Neglecting the areas occupied by the thickness of the dividing wall and the thickness of the column walls, the area of any horizontal cross-section of the column is thus divided between the feed-side portion and the sidedraw-side portion. The division of the column's horizontal cross-section between these two portions is not necessarily equal. The division depends on the composition of the feed and on the proportion of the feed that is in the vapor phase. The area of the feed-side portion is generally from about 20% to about 80%, and preferably from about 35% to about 45% of the area of any horizontal cross-section. Accordingly, the area of the sidedraw-side portion is generally from about 20% to about 80%, and preferably from about 55% to about 65% of the area of any horizontal cross-section.

The dividing wall is generally a baffle that is preferably imperforate. The dividing wall may be a single piece or may consist of multiple sectional pieces that are affixed together, such as by welding or bolting. The baffle is generally rectangular having two faces and four edges. One face of the baffle faces the feed-side portion of the middle zone, and the other face faces the sidedraw-side portion. The four edges are arranged in two pairs of generally opposing edges. One pair of edges comprises the side edges of the baffle, and each edge of this pair is affixed to the inside column wall of the middle zone. Preferably, each edge of this pair is sealingly engaged to the inside wall in a manner, such as by seal welding, so that with respect to passing between the attached edge and the column wall, fluids in one portion of the middle zone are not in communication with fluids in the other portion. Neither edge of the other pair of generally opposing edges is attached to the column wall. One of the edges of this other pair is the top edge of the dividing wall and delineates the top of the middle zone and the bottom of the top zone. The other edge is the bottom edge of the dividing wall and delineates the bottom of the middle zone and the top of the bottom zone. None of the four edges is necessarily straight. For example, depending on the contour of the column wall, the side edges may be shaped or rounded in order to facilitate attachment of the dividing wall to the column wall. Also, the top edge may be shaped or segmented in a manner that facilitates attachment or fit-up between the dividing wall and plates or other column internals in the top of the middle zone and/or the bottom of the top zone. Likewise, the bottom edge may be shaped to enhance the fit between the dividing wall and plates or internals at the bottom of the middle zone and/or the top of the bottom zone.

The thickness of the dividing wall may be any suitable thickness, subject to mechanical requirements of the structural strength of the dividing wall, attachment to the column wall, or attachment to other column internals. The thickness of the dividing wall depends on the column diameter, but is usually between ⅜ in and ¾ in (9.5 and 19.1 mm) for column diameters between 6 ft and 36 ft (1.8 and 11.0 m). The dividing wall may comprise two walls with a gas space in between, such as disclosed in U.S. Pat. No. 5,785,819. The dividing wall may be constructed from any suitable material, and it is believed preferable that that the dividing wall and the column wall shell are of the same material. The dividing wall material is usually carbon steel. The surfaces of the faces of the dividing wall are generally smooth. However, either surface may have liquid deflectors, such as disclosed in U.S. Pat. No. 5,785,819.

Vapor-liquid contacting devices are installed on the feed-side portion and the sidedraw-side portions in the middle zone of the dividing wall fractionation column. Any suitable vapor-liquid contacting device may be used. Suitable vapor-liquid contacting devices, including plates and packing, and their performances are described at pages 14–24 to 14–61 of *Perry's Chemical Engineers' Handbook*, $7^{th}$ Edition, edited by D. W. Green et al., published by McGraw-Hill, New York, in 1997. As used herein, the term "plate" includes tray, and suitable trays include those formed from a number of adjacent triangular (v-shaped) downcomers or other multiple downcomers, which are disclosed in U.S. Pat. Nos. 5,262,094, 5,366,666, 5,407,605, 5,554,329, and 5,707,563, the teachings of all of which are incorporated herein by reference. A bed-like layer of packing material may be closely adjacent to the bottom surface of the plate in the so-called "disengagement" zone under the plate. The packing may extend to the tray below.

In the feed-side portion, generally from 3 to about 50 or more plates, and more typically from 3 to about 45 plates, are located above the elevation of the feed inlet and below the elevation of the top edge of the dividing wall, with generally from 3 to about 50 or more plates, and more typically from 3 to about 45 plates, located between the feed inlet and the bottom of the dividing wall. In the sidedraw-side portion, generally from 3 to about 50 or more plates, and more typically from 3 to about 45 plates, are located above the sidedraw outlet and below the top edge of the dividing wall, while generally from 3 to about 50 or more plates, and more typically from 3 to about 45 plates, are located between the sidedraw outlet and the bottom of the dividing wall. Plate spacings in part or parts of the feed-side portion may be the same as or different from not only plate spacings in part or parts of the sidedraw-side portion but also spacings in other part or parts of the feed-side portion. Generally, the spacings for the feed plate and the sidedraw plate are generally greater than spacings for other plates. The plates referred to in this paragraph are assumed to have a plate efficiency of 80%. As used herein, plate efficiency is the approach to equilibrium defined as the ratio of the actual change in vapor composition as the vapor passes through the plate to the change that would have occurred if the vapor had reached a state of equilibrium with the liquid leaving the plate. If plates having a plate efficiency other than 80% are used, a person of ordinary skill in the art of fractionation is able to readily determine the appropriate number of plates.

Vapor-liquid contacting devices are also installed in the top and bottom zones of the dividing wall fractionation column, and any of the previously mentioned gas-liquid contacting devices are suitable for either zone. Generally, from 3 to about 50 plates, and more typically from 3 to about 45 plates, are located in the top zone. The bottom zone contains generally from 3 to about 50 plates, and more typically from 3 to about 45 plates. The plates referred to in this paragraph are assumed to have a plate efficiency of 80%. Usually, the spacing between plates is generally uniform in the top zone or in the bottom zone, but is not necessarily the same in both the top and bottom zones.

Persons of ordinary skill in the art of fractionation are aware that, with all Is other variables constant, the number of plates in a fractionation zone generally varies directly with the V/L ratio. As used herein, the V/L ratio, or simply V/L, is the ratio of moles of upflowing vapor (V) to moles of downflowing liquid (L). The designer of a fractionation zone arrives at the optimum number of plates and the optimum V/L ratio by trading-off or balancing the capital cost of the fractionation column on the one hand with the operating cost on the other hand. To achieve a given separation, the higher the V/L, the greater is the number of plates. This relationship applies within the dividing wall fractionation column to each of the top, middle, and bottom zones; within the middle zone to both the feed-side portion and sidedraw-side portions; within the feed-side portion to the plates above the feed inlet and to those below the feed inlet; and within the sidedraw-side portion to the plates above the sidedraw outlet and to plates below the sidedraw outlet. Accordingly, a person of ordinary skill in the art is aware that the number of plates in a zone, portion, or part of a portion of the dividing wall fractionation column may be more than or less than the numbers of plates set forth above, depending on the V/L in that respective zone, portion, or part of a portion of the column. Where packing is used in a zone, either in addition to or instead of plates, such a zone is usually designed based on the hydraulic performance (e.g., pressure drop, flooding, and loading) and mass transfer performance (e.g., height equivalent to a theoretical plate, or HETP).

The plates above the feed inlet in the feed-side portion function as a rectification section to decrease the concentrations of high-boiling hydrocarbons without significantly decreasing the concentrations of low-boiling hydrocarbons in the upflowing vapor. It is believed that a substantial portion of the high-boiling hydrocarbons that are present in the sidedraw stream are high-boiling hydrocarbons that flow upward in the feed-side portion, reach the top of the dividing wall, flow downward through the plates in the sidedraw-side portion, and ultimately exit in the sidedraw stream. Accordingly, the molar ratio V/L in the feed-side portion above the feed inlet, as well as the temperature at the top of the dividing wall in the feed-side portion, are important parameters for controlling the concentration of high-boiling hydrocarbons in the sidedraw stream. In the feed-side portion above the feed inlet, V/L is generally from about 0.1 to about 10.0.

The plates in the top zone function as a further rectification zone not only to further decrease the concentration of the high-boiling hydrocarbons but also to decrease the concentration of heartcut hydrocarbons generally, and of the light key component in particular, in the upflowing vapor in order to attain a highly concentrated overhead stream comprising low-boiling hydrocarbons. V/L in the top zone is generally from about 0.1 to about 10.0.

The plates below the feed inlet in the feed-side portion act as a stripping section to decrease the concentrations of low-boiling hydrocarbons without significantly decreasing the concentrations of high-boiling hydrocarbons in the downflowing liquid. It is believed that a substantial portion of the low-boiling hydrocarbons that are present in the sidedraw stream are low-boiling hydrocarbons that flow downward in the feed-side portion, reach the bottom of the dividing wall, flow upward through the sidedraw-side portion, and ultimately exit in the sidedraw stream. Accordingly, the V/L in the feed-side portion below the feed inlet, as well as the temperature at the bottom of the dividing wall in the feed-side portion, are important parameters for controlling the concentration of low-boiling hydrocarbons in the sidedraw stream. In the feed-side portion below the feed inlet, V/L is generally from about 0.1 to about 10.0.

The plates in the bottom zone act as a stripping zone not only to further decrease the concentration of low-boiling hydrocarbons but also to decrease the concentration of heartcut hydrocarbons in general, and of the heavy key component in particular, in the downflowing liquid in order to attain a highly concentrated bottom stream comprising high-boiling hydrocarbons. In the bottom zone, V/L is generally from about 0.1 to about 10.0.

The plates above the sidedraw outlet in the sidedraw-side portion act as a stripping section to decrease the concentrations of low-boiling hydrocarbons in the descending liquid. Although not a substantial portion of the low-boiling hydrocarbons that are charged to the column with the feed are present in the sidedraw stream, low-boiling hydrocarbons that flow downward in the sidedraw-side portion above the sidedraw outlet can ultimately exit in the sidedraw stream. The V/L above the sidedraw outlet in the sidedraw-side portion is generally from about 0.1 to about 10.0.

The plates below the sidedraw outlet in the sidedraw-side portion act as a rectification section to decrease the concentrations of high-boiling hydrocarbons in the ascending vapor. Although not a substantial portion of the high-boiling hydrocarbons that enter the column in the feed are present in the sidedraw stream, high-boiling hydrocarbons that flow upward in sidedraw-side portion below the sidedraw outlet can ultimately exit in the sidedraw stream. The V/L below the sidedraw outlet in the sidedraw-side portion is generally from about 0.1 to about 10.0

The sidedraw stream is highly concentrated in the heartcut hydrocarbons. The concentration in the sidedraw stream of hydrocarbons lighter than the light key component is generally less than 2.5 wt-% and preferably less than 500 wt-ppm. The concentration in the sidedraw stream of hydrocarbons heavier than the heavy key component is generally less than 2.5 wt-% and preferably less than 500 wt-ppm. As used herein, the term "recovery" of a hydrocarbon component is computed by dividing the quantity of that component recovered from the dividing wall fractionation column in the sidedraw stream by the quantity of that component charged to the dividing wall fractionation column in the feed, and multiplying by 100. If the engineering units of quantity in the numerator and the denominator are the same, then recovery is dimensionless and is expressed as a percent. The recovery of the light key component is generally greater than 85% and preferably greater than 90%, and the recovery of the heavy key component is generally greater than 85% and preferably greater than 90%.

At least a portion of the overhead stream from the dividing wall fractionation column passes to an overhead condenser, which may be a partial condenser or a total condenser. The outlet of the overhead condenser passes to an overhead receiver, which separates the condensed material from any uncondensed overhead materials. At least a portion of the condensed overhead material is refluxed to the dividing wall fractionation column, preferably to a point above the top plate in the top zone. The net overhead stream from the dividing wall fractionation column may be comprise uncondensed material, condensed material, or a combination of uncondensed and condensed material from the overhead stream.

The overhead condenser may be a contact condenser. Contact condensers have been used in crude oil fractionation, in atmospheric residuum fractionation, and in the rerun column of a kerosene strip-and-rerun fractionation process. In a contact condenser, the condensing medium directly contacts the stream being condensed usually over a vapor-liquid contacting device, such as packing or any of the previously mentioned gas-liquid contacting devices. Although the contact condenser may be external to the column, preferably the contact condenser is located within the column, and usually above the uppermost plate of the top zone. Vapors rising from the uppermost plate of the top zone pass upwardly through the contact condenser and countercurrently to the downward flow of the cooling medium. A net stream of uncondensed vapor is withdrawn from the top of the contact condenser and sent to recovery facilities. A liquid stream comprising condensing medium and condensed vapors is withdrawn from the bottom of the contact condenser. A portion of the liquid stream is withdrawn as a net stream from the bottom of the contact condenser and sent to recovery facilities, and the remaining portion is cooled and recycled to the top of the contact condenser. The contacting medium can comprise the low-boiling hydrocarbons or a portion of the overhead liquid of the fractionation column that is recycled to the fractionation column. The use of a contact condenser is advantageous because the pressure drop for the stream being condensed across a contact condenser is small relative to that across other condensers, which in turn allows the dividing wall fractionation column to operate at a lower pressure.

At least a portion of the bottom stream from the dividing wall fractionation column passes to a reboiler. The reboiler may be an external reboiler or an internal reboiler. A pump may be used to pass the portion of the bottom stream through the reboiler. Alternatively, the reboiler may be a so-called thermal siphon reboiler, in which reboiling changes the density of the material being reboiled and that density change, in turn, induces flow through the reboiler. The outlet stream of the reboiler is generally a two-phase mixture of vaporized material from the bottom stream and unvaporized material. At least a portion of the outlet stream of the reboiler passes to the dividing wall fractionation column, preferably to a point below the bottom plate in the bottom zone. The net bottom stream from the dividing wall fractionation column is generally withdrawn as a portion of the bottom stream prior to passing to the reboiler.

The dividing wall fractionation column may also have one or more reboilers, where each reboiler is located at an elevation above that of at least one of the plates in the bottom zone. Such a reboiler, if any, is generally in addition to, rather than instead of, the reboiler to which the bottom stream from the dividing wall fractionation column passes. Although such a reboiler, if any, may be located at an elevation above the bottom of the dividing wall, it is generally located below the bottom of the dividing wall. When such a reboiler is below the bottom of the dividing wall, the reboiler is thus in the bottom zone, rather than in the feed-side portion or in the sidedraw-side portion. However, when located in the bottom zone, such an additional reboiler is located in an orientation relative to the dividing wall fractionation column so that a substantial portion of the outlet stream from that reboiler passes to only one portion of the dividing wall distillation column. By "a substantial portion of the reboiler outlet stream," it is meant at least 80% and preferably at least 90% of the reboiler outlet stream. Thus, each such reboiler delivers a substantial portion of its outlet stream either to the feed-side portion or to the sidedraw-side portion. In this manner, each such reboiler can deliver a desired amount of reboiled vapor to either portion of the dividing wall fractionation column. Although any such additional reboiler may be an external reboiler, preferably it is an internal reboiler, such as a stab-in reboiler.

The operating pressure of the dividing wall fractionation column may be any suitable pressure at which the relative volatilities of the hydrocarbons to be separated are sufficiently different that the desired separation can be effected by fractionation. The operating pressure is generally from about 7 to about 20 psi(a) (48.3 to 138 kPa(a)). It is believed that, within this operating pressure range, the lower the operating pressure, the lower will be the capital and operating costs of the dividing wall fractionation column.

When using two fully thermally coupled fractionation columns, the feed passes to a prefractionator and the heartcut fraction is recovered in a sidedraw stream from a main column.

As used herein, two fractionation columns are said to be thermally coupled if at least part of the heat transfer that is used for separation in the first column is provided by directly contacting the material being fractionated in the first column with a product stream from the second column. Direct contacting occurs when fluids withdrawn from a location inside the second column (e.g., from a plate, downcomer, packing, liquid sump, vapor space, etc.) are introduced into a location where fluids are present in the first column (e.g., into a plate, downcomer, packing, liquid sump, or vapor space), without first passing through a heat exchanger, such as a condenser or a reboiler. The phrase "without first passing through a heat exchanger" means that the heat content of the fluids entering the first column is generally from 95% to 105%, preferably from 99% to 101%, and more preferably from 99.5 to 100.5%, of the heat content of the fluids withdrawn from the second column. In practice, passing fluid from the second column to the first column results in the transfer of a small amount of heat between the fluid and the ambient surroundings, even if the fluid does not pass through a heat exchanger and even if the fluids are passed through a well-insulated conduit or line. The amount of heat exchanged between the fluid and the ambient surroundings is generally less than 5%, preferably less than 1%, and more preferably less than 0.5%, of the heat content of the fluids.

In a common arrangement of two thermally coupled fractionation columns, instead of each column functioning as a "stand-alone" column with its own reboiler, a vapor stream from a plate (or a downcomer, packing, vapor space, etc.) inside the first column passes through a conduit to the bottom of the second column, and the liquid stream from the bottom of the second column passes through a conduit to a plate (or a downcomer, packing, sump, vapor space, etc.) inside the first column. Thus, the reboiler of the first column provides the reboiling duty for not only the first column but also the second column, and the second column does not have its own reboiler. In another common arrangement, a liquid stream from a plate (or a downcomer, packing, sump, etc.) inside the first column passes through a conduit to the top of the second column, and the vapor stream from the top of the second column passes through a conduit to a plate (or downcomer, packing, sump, vapor space, etc.) inside the first column. In this arrangement, the condenser of the first column provides the condensing duty for the first as well as the second column, and the second column does not have its "own" condenser. Examples of such thermally coupled distillation columns are shown in FIGS. 2(a) and 2(b) of the above-mentioned article by C. Triantafyllou and R. Smith, in Trans IChemE, Vol. 70, Part A, March 1992, 118–132.

FIG. 2(c) of the article by C. Triantafyllou and R. Smith shows an arrangement of two thermally coupled distillation columns that are said to be fully thermally coupled, since one of the columns (the prefractionator) has neither its own condenser nor its own reboiler and the other column (the main column) has both a condenser and a reboiler. The condenser and reboiler of the main column provide the condensing duty and reboiling duty, respectively, not only for the main column but also for the prefractionator. Thus, the vapor stream from the top of the prefractionator passes through a conduit to a plate inside the main column, and a liquid stream from a plate inside the main column passes through a conduit to the top of the prefractionator. Also, the liquid stream from the bottom of the prefractionator passes through a conduit to a plate inside the main column, and a vapor stream from a plate inside the main column passes through a conduit to the bottom of the prefractionator. See also the article by H. Rudd in The Chemical Engineer, Distillation Supplement, Aug. 27, 1992, s14–s15.

When using two fully thermally coupled fractionation columns, the prefractionator separates the feed into a prefractionator overhead vapor stream and a prefractionator bottom liquid stream. In the prefractionator above the feed inlet, the plates act as a rectification section to decrease the concentrations of high-boiling hydrocarbons in the upflowing vapor. There are generally from 3 to about 50 or more plates, and more typically from 3 to about 45 plates, above the elevation of the feed inlet, and the V/L ratio is generally from about 0.1 to about 10. In the prefractionator, below the elevation of the feed inlet, the plates act as a stripping section to decrease the concentrations of low-boiling hydrocarbons without significantly decreasing the concentrations of high-boiling hydrocarbons in the downflowing liquid. There are generally from 3 to about 50 or more plates, and more typically from 3 to about 45 plates, and V/L is generally from about 0.1 to about 10 below the elevation of the feed inlet to the prefractionator. The plates referred to in this paragraph are assumed to have a plate efficiency of 80%. The vapor-liquid contacting devices previously described for use in the dividing wall fractionation column are suitable for use in the prefractionator.

In the main column, the plates above the elevation where the prefractionator overhead vapor stream is introduced and the liquid stream from the main column is withdrawn for the prefractionator help to decrease the concentration of high-boiling hydrocarbons and to decrease the concentration of heartcut hydrocarbons in the upflowing vapors. In this part of the main column, there are generally from 3 to about 50 or more plates, and more typically from 3 to about 45 plates, and V/L is generally from about 0.1 to about 10.0. Below the elevation where the prefractionator overhead vapor is introduced and the liquid stream from the main column is withdrawn for the prefractionator and above the elevation where the sidedraw stream is withdrawn, the plates act as a stripping section to decrease the concentrations of low-boiling hydrocarbons from the descending liquid. There are generally from 3 to about 50 or more plates, and typically from 3 to about 45 plates, in this area of the main column, and V/L is generally from about 0.1 to about 10.0. The area of the main column below the elevation where the sidedraw stream is withdraw and above the elevation where the vapor stream from the main column is withdrawn and the prefractionator bottom liquid stream is introduced acts as a rectification section to decrease the concentrations of high-boiling hydrocarbons in the ascending vapors. This area of the main column generally contains from 3 to about 50 or more plates, and usually from 3 to about 45 plates, and V/L is generally from about 0.1 to about 10.0. In the main column below the elevation where the vapor stream from the main column is withdrawn and the prefractionator bottom liquid stream is introduced, there are generally from 3 to about 50 or more plates, and typically from 3 to about 45 plates. This area of the main column acts as a stripping zone to decrease the concentrations of low-boiling hydrocarbons and of heartcut hydrocarbons, including the heavy key component, and V/L is generally from about 0.1 to about 10.0. The plates referred to in this paragraph are assumed to have a plate efficiency of 80%. Any suitable plate spacing(s) may be used in the main column. The vapor-liquid contacting devices previously described for use in the dividing wall fractionation column are suitable for use in the main column. In a manner similar to that described previously for the dividing wall fractionation column, a person of ordinary skill in the art of fractionation can determine optimum numbers of plates and optimum V/L ratios for the main column, as well for in the prefractionator column.

When using two fully thermally coupled fractionation columns, the composition of the sidedraw stream withdrawn from main column is generally the same as that already described for the sidedraw stream withdrawn from the dividing wall fractionation column. In addition to producing a sidedraw stream, the main column also produces a net overhead stream and a net bottom stream. The composition of the main column's net overhead stream is generally the same as that described previously for the net overhead stream of the dividing wall fractionation column, and the composition of the main column's net bottom stream is generally the same as that described previously for the net bottom stream of the dividing wall fractionation column.

Regardless whether the sidedraw stream is produced by a dividing wall fractionation column or by two fully thermally coupled fractionation columns, the sidedraw stream passes to a zone for the manufacture of alkylbenzenes, which is referred to herein as the alkylbenzene zone. The alkylbenzene zone generally comprises a series of subzones, which together produce the desired alkylbenzene product. Such a series of subzones for the production of LAB is well known to persons of ordinary skill in the art of hydrocarbon processing and need not be described in detail herein. A suitable series of subzones is described in the paper entitled *LAB Production*, by R. C. Schulz, P. R. Pujado, and B. V. Vora, presented at the $2^{nd}$ nd World Conference on Detergents, held at Montreux, Switzerland, during Oct. 5–10, 1986. The teachings of the Schulz et al. paper are hereby incorporated herein by reference.

First, the sidedraw stream generally passes to a hydrotreating subzone in order to remove sulfur and nitrogen contaminants that would otherwise affect the quality of the LAB product or the performance of downstream subzones, which are described hereinafter. The hydrotreating subzone is optional, since it may be omitted if the levels of contaminants in the sidedraw stream are sufficiently low. General practice for LAB production, however, includes the hydrotreating subzone. The particular arrangement of the hydrotreating subzone, such as the hydrotreating reaction conditions, the use of any hydrotreating catalyst, and the routing of process streams within the hydrotreating subzone, is not critical to the success of the subject invention. Further information on suitable hydrotreating subzones may be found in Chapter 8.3 entitled "UOP Unionfining Technology" of the previously mentioned book edited by Meyers. The teachings of Chapter 8.3 are hereby incorporated herein by reference.

The hydrotreated heartcut produced by the hydrotreating subzone passes to a paraffin separation subzone that separates the linear paraffins (normal paraffins) from other hydrocarbons, such as naphthenes, aromatics, and branched paraffins. Branched paraffins are rejected to the extent needed to achieve the desired linearity of the LAB product. Persons of ordinary skill in the art of hydrocarbon processing know of several suitable paraffin separation subzones. The particular arrangement of the paraffin separation subzone, including its flow scheme, any adsorbent, its equipment, and its operating conditions, are not critical to the success of the subject invention. Further information on suitable paraffin separation subzones may be found in Chapter 10.3, entitled "UOP Sorbex Family of Technologies," and Chapter 10.7, entitled "UOP Molex Process for Production of Normal Paraffins," of the previously mentioned book edited by Meyers. The teachings of Chapter 10.3 and 10.7 are hereby incorporated herein by reference.

The paraffin separation subzone product stream comprising normal paraffins passes to a paraffin dehydrogenation subzone that converts paraffins to olefins, and in particular linear paraffins to linear monoolefins. The particulars of the arrangement of the paraffin dehydrogenation subzone, such as the use of any dehydrogenation catalyst, the dehydrogenation reaction conditions, and how process streams flow within the paraffin dehydrogenation subzone, are not critical to the success of the subject invention. The product of the paraffin dehydrogenation subzone comprises a mixture of olefins and unreacted paraffins, since not all of the paraffins convert to olefins in the dehydrogenation subzone. Further information on suitable paraffin dehydrogenation subzones may be found in Chapter 5.2 of the previously mentioned book edited by Meyers.

The olefins, preferably linear monoolefins, produced by the paraffin dehydrogenation subzone pass as in a mixed paraffin-olefin stream to an alkylation subzone, where the olefins alkylate an aromatic compound in the presence of an alkylation catalyst in an alkylation reactor. Although the aromatic compound reactant may be an alkylated derivative of benzene, the preferred aromatic compound reactant for the production of LAB is benzene. While the alkylation catalyst may be a liquid catalyst, such as hydrofluoric acid or sulfuric acid, it is preferably a solid catalyst. Preferred fluorided silica-alumina solid catalysts are disclosed in U.S. Pat. Nos. 5,196,574 and 5,344,997. Additional details on suitable alkylation subzones using solid or liquid catalysts are described in Chapter 1.5 of the previously mentioned book edited by Meyers. The hydrocarbonaceous effluent recovered from the alkylation reactor passes to a product recovery section of the alkylation subzone, which generally comprises at least three columns. The first column, or benzene column, separates the reactor effluent and removes unreacted aromatic compound reactant (e.g., benzene) as an overhead stream for recycle to the alkylation reactor. The second, or paraffin, column removes paraffins from a bottom stream of the benzene column and produces a paraffin-containing overhead stream for recycle to the paraffin dehydrogenation subzone. The third, or LAB, column separates a bottom stream from the paraffin column and produces an overhead stream containing LAB, which is recovered as product. Heavy alkylate is recovered as a bottom stream from the LAB column and may be further separated in a fourth column to recover any LAB present in the LAB column bottom stream.

In additional embodiments of the subject invention, this invention efficiently uses the heat that is removed by the overhead condenser of either the second column (paraffin column) or third column (LAB column) in the product recovery section of the alkylation subzone. The overhead condenser of each column condenses at least a portion of the column's overhead stream in order to produce sufficient liquid for reflux and usually for a net liquid overhead stream. In so doing, the overhead condenser removes a significant amount of heat from each column's overhead stream. It has now been recognized that at least a portion of this heat can be used to provide reboiler duty in the dividing wall fractionation column, rather than rejecting this heat to the atmosphere or to a heat sink, which is not energy efficient. Accordingly, in one embodiment, at least a portion of the overhead stream of the paraffin column is used as the heating medium for a reboiler that delivers vapor to either the feed-side portion or the sidedraw-side portion of the dividing wall fractionation column. In another embodiment, at least a portion of the overhead stream of the LAB column is used as the heating medium for a reboiler that delivers vapor to either the feed-side portion or the sidedraw-side portion of the dividing wall fractionation column.

The reboiler to which some or all of either overhead stream is routed may be the bottom reboiler of the dividing wall fractionation column, one or more of the previously-described additional reboilers of the dividing wall fractionation column, or both. The optimum reboiler for a given overhead stream to exchange heat depends mainly on the difference between the temperature of the overhead stream and the temperature of the fluid being reboiled in the dividing wall fractionation column. For a given surface area for transferring heat, the greater the temperature difference, the more rapidly heat will transfer from the overhead stream to the fluid being reboiled in the dividing wall fractionation column. Alternatively, for a given rate of heat transfer to the fluid being reboiled, the greater the temperature difference, the less is the surface area required for transferring heat. Accordingly, the higher the temperature of the fluid in the dividing wall fractionation column that is being heated by a reboiler, the higher is the temperature of the overhead stream which is passed as the heating medium to that reboiler. The temperature of the overhead stream (heating medium) is greater than the temperature of the fluid being reboiled generally by more than 15° F. (7° C.), and preferably by more than 20° F. (11° C.).

In addition to temperature, another factor influencing the choice of which overhead stream is routed to which reboiler is the flow rate of the overhead stream. For a given overhead stream temperature, the greater the flow rate of the overhead stream, the greater is the amount of heat that can be transferred from the overhead stream. Thus, for a given difference between the temperature of the overhead stream and that of the stream being reboiled, then the greater the desired amount of heat to be transferred, the more preferable it is to use as a heating medium the overhead stream having a greater flow rate.

Figure 2:
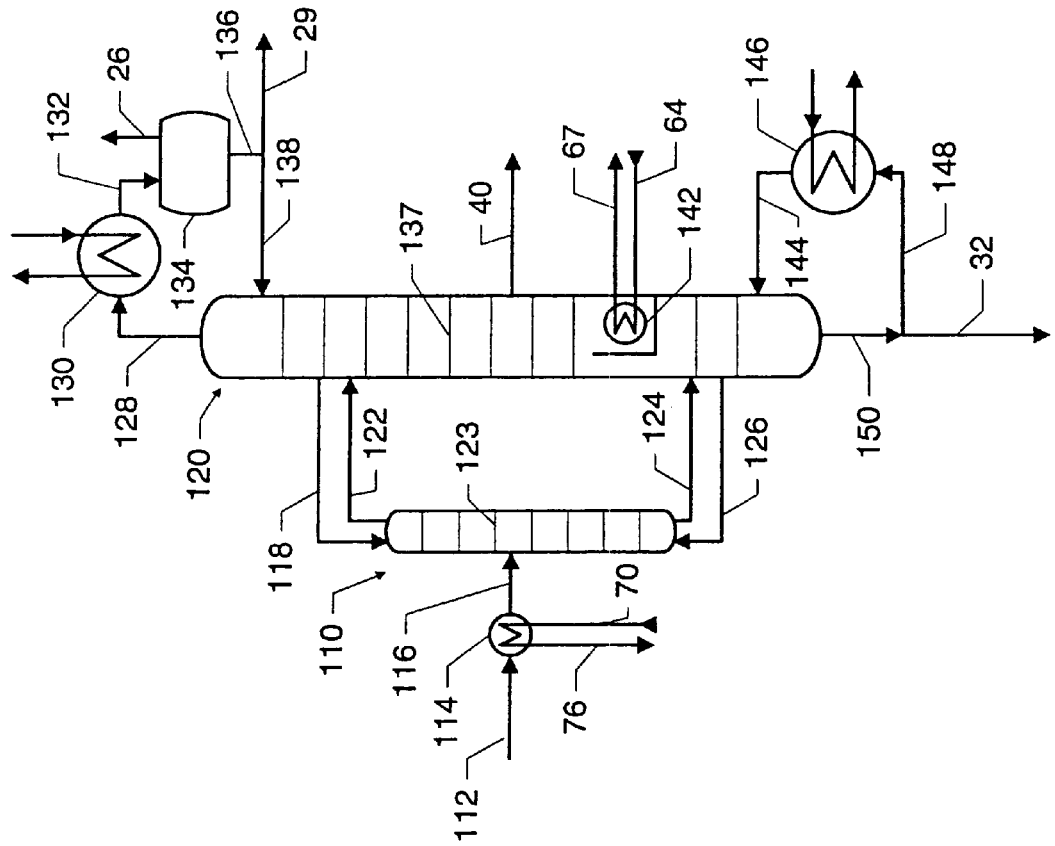

FIGS. 1 and 2 each illustrate a preferred embodiment of the subject invention. FIGS. 1 and 2 are presented solely for purposes of illustration and are not intended to limit the scope of the invention as set forth in the claims. FIGS. 1 and 2 show only the equipment and lines necessary for an understanding of the invention and does not show equipment such as pumps, compressors, heat exchangers, and valves which are not necessary for an understanding of the invention and which are well known to persons of ordinary skill in the art of hydrocarbon processing.

Referring now to FIG. 1, a kerosene boiling range fraction comprising $C_9$ to $C_{15}$ hydrocarbons enters via a line 12 into a dividing wall fractionation column 10. The dividing wall column 10 contains a dividing wall 16 and plates, one of which is designated in FIG. 1 by the item 14. An overhead stream comprising $C_9$ and $C_{10}$ hydrocarbons is recovered from the top of the dividing wall column 10 and passes via line 18 to condenser 20. Using a suitable cooling medium, condenser 20 condenses a portion of the overhead steam and produces a two-phase condenser outlet stream comprising hydrocarbonaceous vapors and liquids. Condenser outlet stream in line 22 enters overhead receiver 24 where the hydrocarbons phase separate into uncondensed vapors which leave receiver 24 via line 26 and condensed liquids which exit receiver 24 via line 27. A portion of the condensed liquids in line 27 refluxes to column 10 via line 28 with the remainder exiting the process via line 29.

A bottom stream comprising $C_{14}$ and $C_{15}$ hydrocarbons is withdrawn from the bottom of column 10 via line 30. A portion of the hydrocarbons in line 30 passes through line 34, is partially vaporized in reboiler 36 using any suitable heating medium, and returns to column 10 as a two-phase reboiler outlet stream via line 38. The remainder of the hydrocarbons in line 30 are rejected from the process via line 32. In addition to external reboiler 36, column 10 is reboiled by two other internal stab-in reboilers, 65 and 74. Stab-in reboiler 74 delivers reboiled vapors to the feed-side portion of dividing wall column 10, while stab-in reboiler 65 provides reboiled vapors to the sidedraw-side portion of column 10. A sidedraw stream comprising $C_{11}$ to $C_{13}$ hydrocarbons is withdrawn from column 10 through line 40 and passes to alkylbenzene zone 80.

Alkylbenzene zone 80 consists of hydrotreating subzone 42, paraffin separation subzone 46, paraffin dehydrogenation subzone 50 and alkylation subzone 90. In hydrotreating subzone 42, a hydrogen-containing stream entering via line 41 reacts with sulfur and nitrogen contaminants in the sidedraw stream in order to produce a hydrotreated heartcut stream having decreased levels of sulfur and nitrogen contaminants in line 44. The hydrotreated heartcut stream enters paraffin separation subzone 46, which produces a raffinate stream comprising naphthenes, aromatics, and branched paraffins which is rejected from the process via line 45. An extract stream comprising linear (normal) paraffins is recovered from the paraffin separation subzone 46 via line 48. The extract stream and a cooled recycle paraffin stream in 67 enter paraffin dehydrogenation subzone 50, which dehydrogenates linear paraffins to linear monoolefins to produce an olefin-containing stream as a primary product flowing through line 52 and a hydrogen-containing stream as a by-product flowing through line 51. Although not shown in FIG. 1, a portion of the hydrogen-containing stream in line 51 may be used to form at least a portion of the hydrogen-containing stream in line 41.

The olefin-containing stream in line 52 and benzene feedstock in line 55 enter alkylation subzone 90, which consists of alkylation reactor 54, benzene column 58, paraffin column 62, and LAB column 68. The benzene feedstock flowing in line 55 combines with a recycle benzene stream 53, in a combined stream of feed and recycle benzene enters alkylation reactor 54 through line 57. In alkylation reactor 54, linear olefins from the olefin-containing stream alkylate benzene from the combined stream to produce linear alkylbenzenes (LAB) which is withdrawn from alkylation reactor 54 via an alkylation reactor effluent stream flowing in line 56. In addition to containing the LAB product, the alkylation reactor effluent stream contains unreacted benzene, paraffins, and heavy alkylbenzene by-products. In benzene column 58, the alkylation reactor effluent stream is separated into a recycle benzene stream comprising benzene which is recovered from the overhead of the benzene column 58 and a benzene column bottom stream depleted in benzene which is recovered from the bottom of benzene column 58 in line 60. The benzene column bottom stream enters paraffin column 62 which separates out paraffins and produces a recycle paraffin stream flowing in line 64 and paraffin column bottom stream which is paraffin-depleted and flows through line 66. The paraffin column bottom stream enters LAB column 68, where the product LAB is recovered in an LAB column overhead stream flowing in line 70. The product LAB comprises alkylbenzenes having an alkyl group having from 11 to 13 carbon atoms. Heavy alkylaromatics, which are defined as alkylaromatics that are heavier than the desired product LAB, comprise alkylbenzenes having an alkyl group having 14 or more carbon atoms. Heavy alkylaromatics are recovered in an LAB column bottom stream which is rejected from the process via line 72.

The recycle paraffin stream in line 64 is the heating medium for internal reboiler 65 in column 10. Recycle paraffin stream 64 may enter reboiler 65 as a vapor-phase stream, a liquid-phase stream, or a mixed-phase vapor-liquid stream. Within reboiler 65, the recycle paraffin stream may or may not undergo a phase change as heat is transferred from the recycle paraffin stream to the fluids in column 10. After having transferred heat through reboiler 65, the now-cooled recycle paraffin stream passes to paraffin dehydrogenation subzone 50 as previously described. The LAB column overhead stream in line 70 is the heating medium for internal reboiler 74 in column 10. On entering reboiler 74, the LAB column overhead stream may be vapor phase, liquid phase, or a mixture of vapor and liquid phases. While transferring heat through reboiler 74 to fluids in column 10, the LAB column overhead stream may or may not undergo a change in phase, such as at least partial condensation from vapor phase to liquid phase. After having transferred heat via reboiler 74, LAB is recovered from the process in an LAB product stream in line 76.

FIG. 2 shows another embodiment of the subject invention wherein the kerosene boiling range fraction feedstock is separated in two fully thermally coupled fractionation columns 110 and 120 rather than in a single dividing wall fractionation column 10 as in FIG. 1. For the sake of brevity, items in FIG. 2 that correspond to items that have already been shown and described in FIG. 1 are not shown in or described in FIG. 2. Items in FIG. 2 that correspond to items in FIG. 1 have the same reference number, such as items numbers 26, 29, 32, 40, 64, 67, 70 and 76.

Referring now to FIG. 2, a kerosene boiling range fraction feedstock enters the process via line 112 and flows into preheat exchanger 114. In exchanger 114, the feedstock is heated by indirect heat exchange with the LAB column overhead stream flowing in line 70. The heated feedstock flows through line 116 and enters prefractionator 110. Prefractionator 110 contains plates, one of which is denoted with item 123. A prefractionator overhead stream is recovered from the top of prefractionator 110 via line 122 and passes to main column 120. A main column liquid draw stream flows from main column 120 to prefractionator 110 via line 118. A prefractionator bottom stream is recovered from the bottom of prefractionator 110 and flow through line 124 to main column 120. A main column vapor draw stream flows from main column 120 to the bottom of prefractionator 110 through line 126. A main column overhead stream comprising $C_9$ and $C_{10}$ hydrocarbons is recovered from the top of main column 120 and passes via line 128 to condenser 130. Condenser 130 uses a suitable cooling medium and condenses a portion of the main column overhead steam and produces a two-phase condenser outlet stream comprising hydrocarbonaceous vapors and liquids. The condenser outlet stream in line 132 enters overhead receiver 134 where the hydrocarbons phase separate into uncondensed vapors which leave receiver 134 via line 26 and condensed liquids which exit receiver 134 via line 136. A portion of the condensed liquids in line 136 refluxes to main column 120 via line 138 with the remainder exiting the process via line 29.

A main column bottom stream comprising $C_{14}$ and $C_{15}$ hydrocarbons is withdrawn from the bottom of main column 120 via line 150. A portion of the hydrocarbons in line 150 passes through line 148, is partially vaporized in reboiler 146 using any suitable heating medium, and returns to main column 120 as a two-phase reboiler outlet stream via line 144. The remainder of the hydrocarbons in line 150 are rejected from the process via line 32. In addition to external reboiler 146, main column 120 is reboiled by internal stab-in reboiler 142. The heating medium for stab-in reboiler 142 is the paraffin recycle stream in line 64, which after being cooled in reboiler 142, flows through line 67 to paraffin dehydrogenation subzone 50. Stab-in reboiler 142 produces reboiled vapors at an elevation in main column 120 above the elevation of the introduction of the prefractionator bottom stream via line 124 and below the elevation of the withdrawal of the sidedraw stream via line 40. The sidedraw stream comprises $C_{11}$ to $C_{13}$ hydrocarbons and passes to alkylbenzene zone 80.

EXAMPLES

The following examples illustrate embodiments of the invention for the separation of a kerosene boiling range fraction comprising $C_9$ to $C_{15}$ hydrocarbons into a light stream comprising low-boiling hydrocarbons comprising $C_9$ and $C_{10}$ hydrocarbons, a sidedraw stream comprising heart-cut hydrocarbons comprising $C_{11}$, $C_{12}$, and $C_{13}$ hydrocarbons, and a heavy stream comprising high-boiling hydrocarbons comprising $C_{14}$ and $C_{15}$ hydrocarbons. The light key component is normal $C_{11}$ paraffin and the heavy key component is normal $C_{13}$ paraffin. In the sidedraw stream in all of the following examples, the concentration of components lighter than normal $C_{11}$ paraffin is less than 2.5 wt-%, and the concentration of components heavier than normal $C_{13}$ paraffin is less than 2.5 wt-%. More than 85 mol-% of the normal $C_{11}$ paraffin, and more than 85 mol-% of the normal $C_{13}$ paraffin, in the feed stream are recovered in the sidedraw stream. These examples are based on engineering calculations and scientific fractionation predictions, and are not intended to limit the invention as set forth in the claims.

Figure 3:
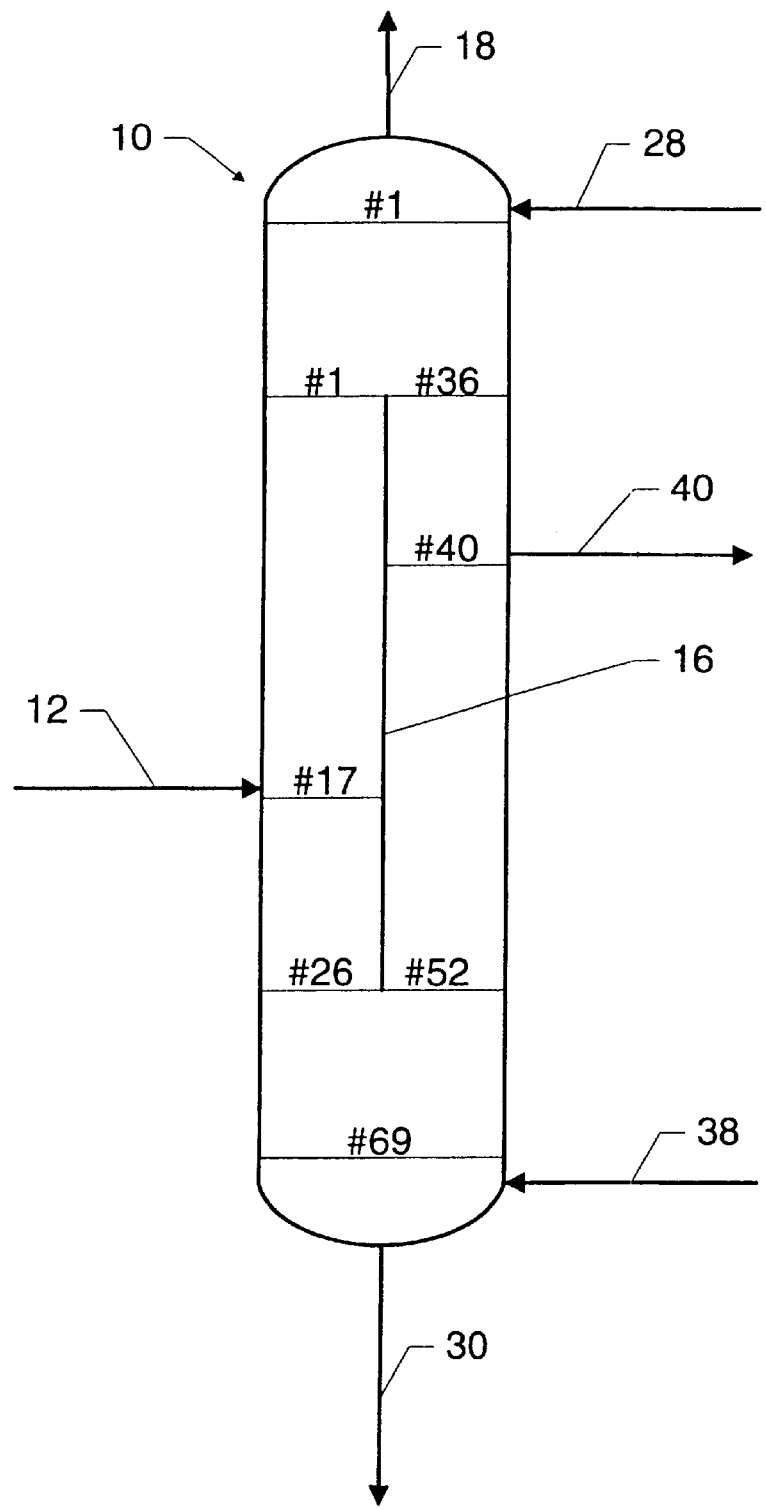

These examples make reference to FIG. 3, which shows a dividing wall fractionation column 10 and which uses the same reference numbers as FIG. 1 to avoid unnecessary repetition. The trays in column 10 in this Example 3 have a plate efficiency of 80%. Tray numbers in FIG. 3 are preceded by a "#" symbol to distinguish them from reference numbers. Two tray numbering systems are used in FIG. 3. One system assigns numbers to trays in the feed-side portion of the middle zone in ascending order from the top to the bottom of the feed-side portion. In this numbering system, the tray at the top of dividing wall 16 is denoted tray #1, fifteen trays (not shown in FIG. 3) are between tray #1 and feed tray #17, and eight trays (not shown) are between the feed tray and tray #26, which is in the feed-side portion of the middle zone at the bottom of dividing wall 16. The other numbering system numbers trays in the top zone, the sidedraw-side portion of the middle zone, and the bottom zone in ascending order from the top to the bottom of dividing wall fractionation column 10. In this second system, the tray that is uppermost in dividing wall fractionation column 10 and which is shown just below line 28 is denoted as tray #1. Further down column 10 and on the sidedraw-side portion of the middle zone, the tray shown at the top of dividing wall 16 is tray #36, the side-draw tray is tray #40, and the tray at the bottom of dividing wall 16 is tray #52. Below the middle zone, this second numbering system continues to tray #69, which is shown just above line 38 and is the lowermost tray in dividing wall fractionation column 10. Thus, thirty-four trays (not shown in FIG. 3) are in the top zone between tray #1 and tray #36. Three trays (not shown) are in the sidedraw-side portion between tray #36 and the side-draw tray #40. Eleven trays (not shown) are in the sidedraw-side portion between the side-draw tray and tray #52. Finally, sixteen trays (not shown) are in the bottom zone between tray #52 and tray #69.

Example 1

Referring now to FIG. 3, a kerosene boiling range fraction comprising $C_9$ to $C_{15}$ hydrocarbons is charged to dividing wall fractionation column 10. The feed temperature is 421° F. (216° C.). In the feed-side portion of the middle zone, V/L is 4.5 between trays #1 and #17, V/L is 0.6 between trays #17 and #26, the temperature at tray #1 is 426° F. (219° C.), and the temperature at tray #26 is 489° F. (254° C.). In the top zone, V/L is 1.2 between uppermost tray #1 and the two trays at the top of divided wall 16, which are tray #1 (feed-side portion) and tray #36 (sidedraw-side portion). In the sidedraw-side portion of the middle zone, V/L is 0.8 between trays #36 and #40, V/L is 1.5 between trays #40 and #52, the temperature at tray #36 is 470° F. (243° C.), and the temperature at tray #52 is 520° F. (271° C.). In the bottom zone, V/L is 0.8 between tray #69 and the two trays at the bottom of divided wall 16, which are tray #26 (feed-side portion) and tray #52 (sidedraw-side portion).

What is claimed is:

1. A process for the production of alkylaromatics, the process comprising:
   a) passing a feed stream comprising low-boiling hydrocarbons, heartcut hydrocarbons, and high-boiling hydrocarbons into a first lateral section of an intermediate portion of a fractionation column at fractionation conditions, and separating the entering compounds to provide an overhead stream comprising the low-boiling hydrocarbons, a sidedraw stream comprising the heartcut hydrocarbons, and a bottom stream comprising the high-boiling hydrocarbons, wherein the first lateral section is separated from a second lateral section of the fractionation column by a vertically oriented baffle extending upward from a lower portion of the fractionation column to an upper portion of the fractionation column;
   b) at least partially condensing the overhead stream to form a condensed stream comprising the low-boiling hydrocarbons, refluxing a portion of the condensed stream to the fractionation column, and recovering the low-boiling hydrocarbons from the overhead stream;
   c) introducing heat to the lower portion of the fractionation column, and withdrawing a bottom stream comprising the high-boiling hydrocarbons from the lower portion of the fractionation column, and recovering the high-boiling hydrocarbons from the bottom stream;
   d) withdrawing a sidedraw stream comprising the heartcut hydrocarbons from the second lateral section of the fractionation column, wherein the heartcut hydrocarbons comprise paraffinic hydrocarbons, and passing at least a portion of the sidedraw stream to a dehydrogenation zone to dehydrogenate the paraffinic hydrocarbons to monoolefinic hydrocarbons, and recovering from the dehydrogenation zone a dehydrogenation zone effluent stream comprising the monoolefinic hydrocarbons; and
   e) passing at least a portion of the dehydrogenation zone effluent stream and an aromatic stream comprising a feedstock aromatic compound to an alkylation zone operated at alkylation conditions to alkylate the feedstock aromatic compound with the monoolefinic hydrocarbons to produce alkylaromatic hydrocarbons, and recovering from the alkylation zone an alkylation effluent stream comprising the alkylaromatic hydrocarbons.

2. The process of claim 1 further characterized in that the sidedraw stream comprises normal paraffinic hydrocarbons, at least a portion of the sidedraw stream passes to a paraffinic separation zone to concentrate the entering normal paraffinic hydrocarbons, a product stream having a first concentration of normal paraffinic hydrocarbons is recovered from the paraffinic separation zone, a paraffinic separation zone effluent stream having a second concentration of normal paraffinic hydrocarbons that is less than the first concentration is recovered from the paraffinic separation zone, and at least a portion of the paraffinic separation zone effluent stream passes to the dehydrogenation zone.

3. The process of claim 2 further characterized in that the sidedraw stream has a first concentration of impurities, at least a portion of the sidedraw stream passes to a hydrogenation zone to hydrogenate at least a portion of the impurities, a hydrogenation zone effluent stream comprising the heartcut hydrocarbons and having a decreased concentration of impurities relative to the sidedraw stream is withdrawn from the hydrogenation zone, and at least a portion of the hydrogenation zone effluent stream passes to the paraffinic separation zone.

4. The process of claim 3 wherein the impurities comprise sulfur or nitrogen.

5. The process of claim 1 wherein the heartcut hydrocarbons comprise $C_{11}$–$C_{13}$ hydrocarbons or $C_{10}$–$C_{12}$ hydrocarbons.

6. The process of claim 1 wherein the low-boiling hydrocarbons comprise $C_9$ hydrocarbons and hydrocarbons lighter than $C_9$ hydrocarbons.

7. The process of claim 1 wherein the high-boiling hydrocarbons comprise $C_{14}$ hydrocarbons and hydrocarbons heavier than $C_{14}$ hydrocarbons.

8. The process of claim 1 further characterized in that the feed stream has a concentration of low-boiling hydrocarbons of more than 5 wt-%.

9. The process of claim 1 further characterized in that the feed stream has a concentration of heartcut hydrocarbons of more than 50 wt-%.

10. The process of claim 1 further characterized in that the feed stream has a concentration of high-boiling hydrocarbons of more than 5 wt-%.

11. The process of claim 1 further characterized in that the heartcut hydrocarbons comprise a heavy key compound and the sidedraw stream has a concentration of hydrocarbons heavier than the heavy key compound of less than 2.5 wt-%.

12. The process of claim 1 further characterized in that the heartcut hydrocarbons comprise a heavy key compound and the sidedraw stream has a concentration of hydrocarbons heavier than the heavy key compound of less than 500 wt-ppm.

13. The process of claim 1 further characterized in that the heartcut hydrocarbons comprise a light key compound and the sidedraw stream has a concentration of hydrocarbons lighter than the light key compound of less than 2.5 wt-%.

14. The process of claim 1 further characterized in that the heartcut hydrocarbons comprise a light key compound and the sidedraw stream has a concentration of hydrocarbons lighter than the light key compound of less than 500 wt-ppm.

15. The process of claim 1 further characterized in that the feed aromatic hydrocarbon comprises benzene and the alkylaromatic hydrocarbons in the alkylation effluent stream comprise alkylbenzenes, wherein the alkylbenzenes having an alkyl group having from 11 to 13 carbon atoms.

16. The process of claim 1 further characterized in that the alkylation effluent stream comprises the paraffinic hydrocarbons, and the recovering of the alkylation effluent stream from the alkylation zone comprises passing the alkylation effluent stream to a product separation zone, separating the alkylation effluent stream in the product separation zone into a paraffin recycle stream comprising the paraffinic hydrocarbons and a product stream comprising the alkylaromatic hydrocarbons.

17. The process of claim 16 further characterized in that the introduction of heat to the lower portion of the fractionation column comprises indirectly exchanging heat from at least a portion of the paraffin recycle stream or at least a portion of the product stream to hydrocarbons in the lower portion of the fractionation column.

18. The process of claim 1 further characterized in that the at least partially condensing of the overhead stream comprises directly contacting the overhead stream with a condensing medium.

19. The process of claim 18 further characterized in that the condensing medium directly contacts the overhead stream in the fractionation column.

20. A process for the production of alkylaromatics, the process comprising:
   a) passing a feed stream comprising low-boiling hydrocarbons, heartcut hydrocarbons, and high-boiling hydrocarbons into a prefractionator fractionation column which separates entering hydrocarbons to provide a prefractionator overhead vapor stream comprising the low-boiling hydrocarbons and the heartcut hydrocarbons and a prefractionator bottom liquid stream comprising the high-boiling hydrocarbons and the heartcut hydrocarbons;
   b) passing at least a portion of the prefractionator overhead vapor stream to a main fractionation column, wherein the prefractionator fractionation column and the main fractionation column are fully thermally coupled;
   c) passing at least a portion of the prefractionator bottom liquid stream to the main fractionation column;
   d) separating hydrocarbons in the main fractionation column, and recovering from the main fractionation column a main column overhead stream comprising the low-boiling hydrocarbons, a main column bottom stream comprising the high-boiling hydrocarbons, a main column product sidedraw stream comprising the heartcut hydrocarbons, a main column upper sidedraw stream comprising the low-boiling hydrocarbons and the heartcut hydrocarbons, and a main column lower sidedraw stream comprising the heartcut hydrocarbons and the high-boiling hydrocarbons;
   e) passing at least a portion of the main column upper sidedraw stream to the prefractionator fractionation column;
   f) passing at least a portion of the main column lower sidedraw stream to the prefractionator fractionation column;
   g) at least partially condensing the main column overhead stream to form a condensed stream comprising the low-boiling hydrocarbons, refluxing a portion of the condensed stream, and recovering the low-boiling hydrocarbons from the main column overhead stream;
   h) introducing heat to a lower portion of the main fractionation column, and recovering the high-boiling hydrocarbons from the main column bottom stream;
   i) passing at least a portion of the sidedraw stream to a dehydrogenation zone to dehydrogenate the paraffinic hydrocarbons to monoolefinic hydrocarbons, and recovering from the dehydrogenation zone a dehydrogenation zone effluent stream comprising the monoolefinic hydrocarbons; and
   j) passing at least a portion of the dehydrogenation zone effluent stream and an aromatic stream comprising a feed aromatic hydrocarbon to an alkylation zone operated at alkylation conditions to alkylate the feed aromatic hydrocarbon with the monoolefinic hydrocarbons to produce an alkylation effluent stream comprising alkylaromatic hydrocarbons, and recovering the alkylaromatic hydrocarbons from the alkylation effluent stream.

21. The process of claim 20 wherein the heartcut hydrocarbons comprise $C_{11}$–$C_{13}$ hydrocarbons or $C_{10}$–$C_{12}$ hydrocarbons.

22. The process of claim 20 wherein the low-boiling hydrocarbons comprise $C_9$ hydrocarbons and hydrocarbons lighter than $C_9$ hydrocarbons.

23. The process of claim 20 wherein the high-boiling hydrocarbons comprise $C_{14}$ hydrocarbons and hydrocarbons heavier than $C_{14}$ hydrocarbons.

* * * * *